(12) United States Patent
Leconte et al.

(10) Patent No.: US 8,119,838 B2
(45) Date of Patent: Feb. 21, 2012

(54) CONVERSION OF NITRILE COMPOUNDS INTO CARBOXYLIC ACIDS AND CORRESPONDING ESTERS THEREOF

(75) Inventors: Philippe Leconte, Meyzieu (FR); Cyril Denis, Lyons (FR)

(73) Assignee: Rhodia Operations, Aubervilliers Cedex (FR)

( * ) Notice: Subject to any disclaimer, the term of this patent is extended or adjusted under 35 U.S.C. 154(b) by 162 days.

(21) Appl. No.: 12/308,176

(22) PCT Filed: May 25, 2007

(86) PCT No.: PCT/FR2007/000875
§ 371 (c)(1),
(2), (4) Date: Aug. 28, 2009

(87) PCT Pub. No.: WO2007/141404
PCT Pub. Date: Dec. 13, 2007

(65) Prior Publication Data
US 2009/0326260 A1 Dec. 31, 2009

(30) Foreign Application Priority Data
Jun. 9, 2006 (FR) ................................ 06 05119

(51) Int. Cl.
*C07C 55/00* (2006.01)
(52) U.S. Cl. ...................................... 562/590
(58) Field of Classification Search .............. None
See application file for complete search history.

(56) References Cited

U.S. PATENT DOCUMENTS

| | | | |
|---|---|---|---|
| 2,388,813 A | 11/1945 | Allen et al. | |
| 2,548,025 A | 4/1951 | Jones | |
| 3,567,749 A | 3/1971 | Neugebauer et al. | |
| 3,876,691 A | 4/1975 | Lincoln et al. | |
| 3,991,100 A * | 11/1976 | Hochberg | 560/204 |
| 4,408,067 A | 10/1983 | Nakamura et al. | |
| 6,281,383 B1 | 8/2001 | Korb et al. | |
| 6,664,413 B1 * | 12/2003 | Cockrem | 560/204 |
| 2002/0173433 A1 | 11/2002 | Beatty | |

FOREIGN PATENT DOCUMENTS

| | | | |
|---|---|---|---|
| BE | 687 139 A | | 3/1967 |
| DE | 730518 | | 1/1943 |
| GB | 1122448 | * | 8/1968 |

OTHER PUBLICATIONS

Laeckmann et al., "Synthesis and Biological Evaluation of Aroylguanidines Related to Amiloride as Inhibitors of the Human Platelet Na+/H+ Exchanger", Bioorganic & Medicinal Chemistry, 2002, pp. 1793-1804, vol. 10, No. 6, United Kingdom.
Xue et al., "Transformation of Amides into Esters by the Use of Chlorotrimethylsilane", Journal of the Chinese Chemical Society, 2004, pp. 359-362, vol. 51, No. 2, Taipei, Taiwan.
Fallahpour, "Synthesis of an Isotopically Isomeric Mixture of 1,4,6,8-Tetramethyl [$^{13}C_2$] Azulene and its Thermal Reaction with Dimethyl Acetylenedicarboxylate" *Helvetica Chimical Acta* 1995 vol. 78 No. 6 pp. 1419-1436 XP009082874.
Hanschke, "Zur Kenntnis der Prinsschen Reaktion, II. Mitteil. $^1$): Über die Umsetzung von Butylen mit Formaldehyd" *Chem. Ber.* 1995 No. 88 pp. 1048-1053 XP009082873.
Allinger, "The Relative Stabilities of cis and trans Isomers. IV. The 3,5-Dimethylcycloheptanones" *J. Am. Chem. Soc.* 1959 vol. 81 pp. 232-235 XP002430861.
International Research Report, PCT/FR2007/000875 dated Oct. 19, 2007.

* cited by examiner

*Primary Examiner* — Paul A Zucker
(74) *Attorney, Agent, or Firm* — Buchanan Ingersoll & Rooney PC

(57) ABSTRACT

Hydrocarbon-based compounds containing at least one nitrile function are converted into compounds containing at least one carboxylic function, and into ester compounds from the carboxylic compounds thus obtained; such conversion entails reacting the nitrile compound with a hydroxyl basic compound in solution in a solvent at a temperature of between 80 and 150° C., in eliminating the ammonia formed, in reacting the salt obtained with a mineral acid, and then in recovering the compound containing at least one carboxylic function and, optionally, esterifying the acids obtained by reaction with an alcohol.

23 Claims, No Drawings

CONVERSION OF NITRILE COMPOUNDS INTO CARBOXYLIC ACIDS AND CORRESPONDING ESTERS THEREOF

This application is a continuation of PCT/FR 2007/000875 filed May 25, 2007 and designating the United States, published in the English language as WO 2007/141404 A1, on Dec. 13, 2007, and claiming benefit under 35 U.S.C. 119 of FR 2006/05119, filed Jun. 9, 2006, each hereby expressly incorporated by reference in its entirety and each assigned to the assignee hereof.

The present invention relates to a process for converting hydrocarbon compounds comprising at least one nitrile functional group to compounds comprising at least one carboxyl functional group and also to a process for obtaining ester compounds from these carboxylic compounds thus obtained.

The invention relates more particularly to a process for the conversion of the dinitrile compounds obtained as products and byproducts in the hydrocyanation of butadiene, such as methylglutaronitrile, ethylsuccinonitrile and optionally adiponitrile or the mixture of these three compounds, to diacid compounds, on the one hand, and diester compounds, on the other hand.

The process for the manufacture of adiponitrile by hydrocyanation of butadiene has been made use of industrially for several decades. This process exhibits a high selectivity for adiponitrile, an important chemical intermediate in the synthesis of hexamethylenediamine or caprolactam and the manufacture of polyamides.

However, this process also produces branched dinitrile compounds, such as methylglutaronitrile or ethylsuccinonitrile, in particular, which are separated and recovered by distillation.

Generally, this recovery of the branched dinitrile compounds makes it possible to produce a mixture comprising predominantly methylglutaronitrile with ethylsuccinonitrile and adiponitrile.

Several solutions have been provided for recovering in value these byproducts or mixtures. One of these consists in hydrogenating the dinitrile compounds to give primary amines, in particular for producing methylpentamethylenediamine (MPMD), used as monomer in the manufacture of specific polyamides. This process requires stages for purification either of the methylglutaronitrile or the methylpentamethylene-diamine.

Industrially, these byproducts are often destroyed by combustion with recover in value in the form of steam or energy but with production of gaseous effluents comprising $CO_2$ and nitrogen oxides.

There thus exists a need and a major demand to find novel routes for recovering in value and converting these dinitrile compounds or mixtures to chemical compounds which can be recovered in value and which are economically advantageous.

One of the aims of the present invention is in particular to provide a process which makes it possible to convert these nitrile compounds to carboxylic compounds, on the one hand, which can be used in particular as chemical intermediates, such as, for example, monomers in the manufacture of polyurethanes and polyamides, or to diester compounds, on the other hand, which can be used in particular as solvent.

To this end, the invention provides a process for the conversion of compounds comprising at least one nitrile functional group to compounds comprising at least one carboxyl functional group which consists in reacting the nitrile compound with a basic hydroxyl compound in solution in a solvent at a temperature of between 80 and 200° C., preferably between 80 and 150° C., in removing the ammonia formed, in reacting the salt obtained with an inorganic acid and in then recovering the compound comprising at least one carboxyl functional group.

According to a preferred characteristic of the invention, the basic hydroxyl compound is an alkali metal hydroxide, such as sodium hydroxide, potassium hydroxide or the like.

Advantageously, an aqueous solution of this basic hydroxyl compound is used.

The concentration of basic compounds in the aqueous solution is advantageously between 5 and 30% by weight.

According to a novel advantageous characteristic of the invention, the basic hydroxyl compound is employed with an excess of 3 to 20%, advantageously between 3 and 10%, with respect to the stoichiometric amount necessary to convert the nitrile functional groups to carboxyl functional groups.

The reaction is carried out either at atmospheric pressure, advantageously at a temperature which makes it possible to have reflux of the solvent, for example water, or under pressure with removal of the ammonia formed or without removal of this ammonia formed, which will be dissolved at least partially in the reaction medium.

In one embodiment of the invention, the process is carried out continuously. The reaction with the alkali metal compound can be carried out in a single plug-flow reactor or in several stirred reactors arranged in series. The reaction is advantageously carried out in a device comprising two successive and separate reaction regions, a first region operating under stirred conditions and a second final region operating under plug-flow conditions. The presence of these two reaction regions makes it possible to obtain complete conversion of the nitrile functional groups to carboxyl functional groups. This complete conversion makes it possible to facilitate the recovery and separation of the carboxyl compounds, in particular when the nitrile compounds to be converted are dinitrile compounds, and thus to avoid the presence of cyano and/or amide compounds in the final reaction medium. Thus, the process can be carried out in a device comprising a stirred reactor, equipped with a condenser in order to obtain reflux and a device which recovers the ammonia formed, and a plug-flow reactor arranged in series with the stirred reactor. The stirred reactor can also operate under pressure without separation of the ammonia formed with dissolution of the latter in the reaction medium.

The first stirred reactor can advantageously be a loop reactor, comprising an internal circulation loop and an external circulation loop. A heat exchanger is advantageously provided on the external circulation loop.

Of course, other types of stirred reactors may be used.

Advantageously, the temperatures and the pressures in the stirred reactor and the plug-flow reactor can be different. The plug-flow reactor advantageously operates adiabatically. Preferably, the reaction temperature in the plug-flow reactor is higher than that present in the stirred reactor. Thus, the temperature of the plug-flow reactor is advantageously greater than 100° C., preferably between 100° C. and 200° C.

In the case of a batchwise process, the operating conditions of the reactor are determined in order to advantageously obtain a degree of conversion of the nitrile functional groups of 100%.

The reaction medium on departing from the reaction stage, in particular on departing from the plug-flow reactor, comprises a carboxylate compound of the metal element introduced with the alkali metal compound, advantageously a sodium carboxylate or a potassium carboxylate, and also the ammonia formed, which is dissolved.

This reaction medium is fed to a stage which makes it possible to separate the ammonia formed, for example to a distillation column or a flash distillation device.

The ammonia thus recovered can be directly recovered in value or can be purified, for example by distillation, to separate the water and to obtain ammonia which can be recovered in value, for example in the processes for the manufacture of nitric acid or hydrocyanic acid.

According to one characteristic of the invention, the reaction medium is subsequently acidified by addition of an inorganic acid in order to obtain the carboxylic compound in the protonated form, also known hereinafter as carboxylic acid.

Mention may be made, as inorganic acid suitable for the invention, of sulfuric acid, hydrochloric acid, organic acids exhibiting a pKa of less than or equal to 3, or their mixtures.

Optionally, in order to avoid precipitation of the salts, water can be added to the medium, preferably before the addition of the inorganic acid. The amount of water added is determined in order to obtain a concentration of salt in the reaction medium close to the saturating concentration of the salt in the water.

This acidification is carried out in any type of reactor, in particular in stirred reactors or in line or in a tubular reactor with static mixers.

The amount of acid added is advantageously substantially equal to the amount necessary to neutralize the basic compound added in the first stage.

The reaction medium is subsequently treated in order to recover this carboxylic acid. The reaction medium can be concentrated by evaporation of the water and the salt is separated by filtration.

Preference is given, as treatment process suitable for the invention, to the liquid/liquid extraction of the carboxylic acid by a water-immiscible solvent.

Mention may be made, as extraction solvent suitable for the invention, of water-insoluble polar solvents, such as, for example, ketones, ethers and esters. Mention may be made, as suitable solvent, of methyl isobutyl ketone, diisopropyl ether, methyl tert-butyl ether, ethyl acetate, isopropyl acetate, butyl acetate, diester solvents or the like.

The carboxylic acids are recovered in the phase comprising the extraction solvent and are separated from the solvent, advantageously by distillation of the latter. Solvents forming a heterogeneous azeotrope with water, thus entraining the water present in the extraction phase, are preferred. Thus, the diacids recovered at the bottom of the column for separation of the extraction solvent do not comprise water or simply a very small amount of water. The extraction solvent is advantageously recycled to the extraction stage after separation of the water, for example by settling.

According to another characteristic of the invention, the aqueous phase recovered after extraction of the carboxylic acid, which comprises the salts of the inorganic acid, can be subjected, before discharge as effluent, to a stripping operation in order to recover and extract the traces of extraction solvent.

The carboxylic acids thus obtained are, in one embodiment of the invention, purified by the usual techniques, namely crystallization, distillation, refining or the like.

Thus, it is advantageous to subject the carboxylic acids recovered to a distillation in one or more columns in order to remove, on the one hand, the light compounds and, on the other hand, the heavy products. This purification is simplified if the starting nitrile compounds, in particular methylglutaronitrile, are purified by separation of the volatile compounds, such as cresol and/or pentenenitriles. This purification is also facilitated if the concentration of ammonia in the acids to be purified is very low, thus limiting the formation of salts, such as ammonium sulfate.

It can be advantageous, prior to the purification by distillation, crystallization or refining of the carboxylic acids, to treat them with carbon black or to subject them to a hydrogenation or any other normal purification treatment. These purification treatments can be carried out with the solution of carboxylic acid in the extraction solvent.

After purification, the acids recovered are formed in order to be used in other processes. Mention may be made, as forming process, of flaking, granulation or extrusion in the rod form.

In the case where the nitrile compounds are composed of the byproducts resulting from the hydrocyanation of butadiene, that is to say methylglutaronitrile or a mixture of methylglutaronitrile, ethylsuccinonitrile and adiponitrile, the carboxylic acids recovered are either methylglutaric acid or a mixture of methylglutaric acid, ethylsuccinic acid and adipic acid. Such diacids can have numerous applications, in particular as monomers or comonomers in the manufacture of polyamides, polyesters and polyurethanes or as additives.

According to another embodiment of the invention, the carboxylic acids recovered after separation of the extraction solvent are used in the manufacture of diesters. This embodiment is advantageous in particular when the carboxylic acids result from the conversion of the products obtained by hydrocyanation of butadiene, in particular the methylglutaronitrile, ethylsuccinonitrile and adiponitrile mixture. In this case, the products obtained are diesters and will be referred to generically in the present text as "diesters".

For the manufacture of these diesters, the diacids recovered, before or after purification, are mixed with an alcohol. Esterification is carried out by heating the mixture in the presence of an acid compound in order to catalyze the reaction.

Thus, this reaction can be carried out by passing over a sulfonic acid resin at a temperature of between 40 and 100° C. The medium resulting from the column comprising the resin is subsequently distilled in order to separate the unreacted alcohol and the water formed.

It can also be carried out in a reactive distillation column which makes it possible to carry out the esterification reaction simultaneously with the extraction of the water formed by distillation. Thus, it is possible to shift the equilibrium in order to obtain a degree of conversion in the vicinity of 100%.

The suitable alcohols are, for example, linear or branched and cyclic or noncyclic aliphatic alcohols which can comprise an aromatic nucleus and which can comprise from 1 to 20 carbon atoms. Mention may be made, as preferred examples, of the following alcohols: methanol, propanol, isopropanol, benzyl alcohol, ethanol, n-butanol, isobutanol, cyclohexanol, hexanol, isooctanol, 2-ethylhexanol, pentanols, methylbutanol or the like.

The medium comprising the diesters is subsequently advantageously distilled in a plant comprising a topping and tailing stage. This distillation can be carried out in a single column with recovery of the diesters in the form of an intermediate fraction.

Advantageously, the heavy fraction recovered comprises the monoester compounds, which are at least partially recovered and recycled in the esterification stage. The diesters thus obtained can be used in numerous applications, such as as solvent in paints, varnishes or lacquers, the industry for the coating of surfaces or any other article, such as cables, for example, the industry of inks, lubricants for textiles, binders and resins for cores of casting molds, cleaning products or cosmetic formulations. It can also be used as starting materials in certain chemical reactions or in compositions for treating soils and plants.

More generally, they can be used, alone or in a formulation, as cleaning, stripping or degreasing solvent in any industrial or domestic activity.

These diesters can also be used as plasticizers for certain plastics or as monomers in the manufacture of polymers.

Other advantages and details of the invention will become more clearly apparent in the light of the examples given below solely by way of indication.

Basic Hydrolysis of Dinitrile Compounds:

108 g of a mixture of dinitrile compounds originating from the manufacture of adiponitrile by hydrocyanation of butadiene are added with stirring in 30 min to 560 g of a 15% aqueous sodium hydroxide solution heated beforehand to 80° C.

The mixture of dinitriles has the following composition by weight:

Methylglutaronitrile (MGN): 84.2%
Ethylsuccinonitrile (ESN): 11%
Adiponitrile (AdN): 4%

The remainder to 100% corresponds to various impurities not comprising nitrile functional groups.

The mixture is subsequently heated in order to obtain reflux and is held at this temperature for approximately 7 h.

The ammonia which is given of is recovered and trapped.

The progress of the reaction is monitored by potentiometric titration with a hydrochloric acid solution. This titration makes it possible to determine the remaining amount of sodium hydroxide, the amount of dissolved ammonia and the amount of salified carboxyl functional group corresponding to the various jumps in pH observed during titration.

The yield of hydrolysis is given by the following formula:

$$DC\% = V_{COONa} \times 100 / (V_{NaOH} + V_{COONa}) \times NaOH\ i/MGN\ i$$

in which:

$V_{COONa}$ corresponds to the volume of HCl solution necessary to neutralize the salified carboxyl functional groups, $V_{NaOH}$ corresponds to the volume of HCl solution necessary to neutralize the residual sodium hydroxide, NaOH i corresponds to the initial number of moles of NaOH, MGN i corresponds to the initial number of moles of dinitrile compounds, DC is the degree of conversion of the dinitrile compounds to carboxylic acid.

The reaction is considered to be complete when DC% is approximately 100%.

The reaction medium is subsequently cooled to ambient temperature and 80 g of water are added before running in 105 g of 98% sulfuric acid. The pH of the aqueous solution is of the order of 3.

The aqueous phase is subsequently extracted with 3 times 200 ml of MTBE (methyl tert-butyl ether) at 40° C. The organic phases are combined and the MTBE is subsequently distilled off. 141.6 g of diacids are obtained with a purity, determined by potentiometric titration, of the order of 98.5%.

Esterification

The 141.6 g of crude diacids are dissolved in 621 g of methanol. This solution is subsequently placed in a round-bottomed flask comprising 115 g of sulfonic resin (sold by Röhm & Haas under the name Amberlyst 36 DRY) washed beforehand with methanol.

The combined mixture is brought to reflux for 6 h.

The acid functional groups are titrated by potentiometry with sodium hydroxide, showing that the degree of conversion reaches 95%.

After cooling, the resins are separated by filtration and washed 3 times with 150 ml of methanol. The various methanol phases are combined.

The methanol and the water formed during the esterification are separated by distillation.

The crude diesters are subsequently distilled at 105° C. under 20 mbar on a packed column. A yield of diesters of 93% is obtained with a purity, determined by chromatographic analysis, of greater than 99%.

What is claimed is:

1. A process for the conversion of compounds comprising at least one nitrile functional group to compounds comprising at least one carboxyl functional group, the process comprising:

reacting a mixture of methylglutaronitrile, ethylsuccinonitrile and adiponitrile, with a basic hydroxyl compound in the presence of a solvent at a temperature ranging from 80° C. to 200° C., in order to obtain a mixture of salts of methylglutaric, ethylsuccinic and adipic acids, removing the ammonia formed from the reaction medium, reacting the salts formed with an inorganic acid, and separating the mixture of methylglutaric acid, ethylsuccinic acid and adipic acid thus prepared.

2. The process as defined by claim 1, said basic hydroxyl compound being selected from the group consisting of sodium hydroxide and potassium hydroxide.

3. The process as defined by claim 1, said basic hydroxyl compound comprising an aqueous solution thereof, with a concentration by weight of basic compound ranging from 5% to 30%.

4. The process as defined by claim 1, wherein the amount of basic hydroxyl compound employed constitutes from 103% to 120% of the stoichiometric amount of basic compound, calculated with respect to the amount of the mixture of methylglutaronitrile, ethylsuccinonitrile and adiponitrile to be converted.

5. The process as defined by claim 1, wherein the reaction between the mixture of methylglutaronitrile, ethylsuccinonitrile and adiponitrile and the basic hydroxyl compound is carried out at reflux of the solvent or under pressure.

6. The process as defined by claim 1, wherein the reaction between the mixture of methylglutaronitrile, ethylsuccinonitrile and adiponitrile and the basic hydroxyl compound is carried out batchwise.

7. The process as defined by claim 1, wherein the reaction between the mixture of methylglutaronitrile, ethylsuccinonitrile and adiponitrile and the basic hydroxyl compound is carried out continuously.

8. The process as defined by claim 7, wherein the reaction between the mixture of methylglutaronitrile, ethylsuccinonitrile and adiponitrile and the basic hydroxyl compound is carried out in apparatus comprising two successive and separate reaction regions:

a first region operating under stirred conditions, a second region operating under plug-flow conditions.

9. The process as defined by claim 1, wherein the amount of inorganic acid is at least equal to the stoichiometric amount calculated in order to neutralize the basic hydroxyl compound.

10. The process as defined by claim 1, wherein the inorganic acid is selected from the group consisting of hydrochloric acid, sulfuric acid, organic acids having a pKa of less than or equal to 3, and mixture thereof.

11. The process as defined by claim 1, wherein separation of the carboxylic compound obtained is carried out by liquid/liquid extraction.

12. The process as defined by claim 11, wherein the liquid/liquid extraction is carried out with an extraction solvent selected from water-insoluble polar solvents.

13. The process as defined by claim 12, wherein the extraction solvent is selected from the group consisting of ketones, ethers and esters.

14. The process as defined by claim 13, wherein the extraction solvent is selected from the group consisting of methyl isobutyl ketone, diisopropyl ether, methyl tert-butyl ether, ethyl acetate, isopropyl acetate, butyl acetate and diesters.

15. The process as defined by claim 11, wherein the carboxylic compounds extracted are separated from the extraction solvent by distillation.

16. The process as defined by claim 1, wherein the carboxylic compounds recovered are purified by distillation, crystallization or refining.

17. The process as defined by claim 1, wherein the carboxylic compound(s) obtained are converted into esters by reaction with an alcohol.

18. The process as defined by claim 17, wherein said alcohol is selected from the group consisting of linear or branched and cyclic or noncyclic aliphatic alcohols which can contain an aromatic nucleus and which has from 1 to 20 carbon atoms.

19. The process as defined by claim 18, wherein said alcohol is selected from the group consisting of methanol, propanol, isopropanol, benzyl alcohol, ethanol, n-butanol, isobutanol, cyclohexanol, hexanol, isooctanol, 2-ethylhexanol, pentanol isomers and isobutanol.

20. The process as defined by claim 17, wherein the esterification reaction is carried out in the presence of $H^+$ ions.

21. The process as defined by claim 17, wherein the esterification reaction is carried out in a reactive column with removal of water.

22. The process as defined by claim 17, wherein the esterification reaction is carried out by passing the carboxylic compound/alcohol mixture over a sulfonic acid ion-exchange resin.

23. The process as defined by claim 17, wherein the esters formed are recovered and purified by distillation.

* * * * *